United States Patent [19]

Wildung et al.

[11] Patent Number: 6,150,155
[45] Date of Patent: Nov. 21, 2000

[54] KIT FOR PROVIDING A TECHNETIUM MEDICAL RADIOIMAGING AGENT

[75] Inventors: Raymond E. Wildung, Richland, Wash.; Thomas R. Garland, Greybull, Wyo.; Shu-Mei W. Li, Richland, Wash.

[73] Assignee: Battelle Memorial Institute, Richland, Wash.

[21] Appl. No.: 09/397,784

[22] Filed: Sep. 16, 1999

Related U.S. Application Data

[63] Continuation-in-part of application No. 09/099,680, Jun. 18, 1998, abandoned.

[51] Int. Cl.[7] .................................................. C12N 5/00
[52] U.S. Cl. .................. 435/252.1; 424/1.11; 430/56; 430/270.1; 435/29; 435/41; 435/257.1
[58] Field of Search ..................................... 435/252.1, 29, 435/257.1, 41; 430/56, 270.1; 424/1.11

Primary Examiner—Leon B. Lankford, Jr.
Attorney, Agent, or Firm—Paul W. Zimmerman

[57] ABSTRACT

The present invention is directed toward a kit for microbial reduction of a technetium compound to form other compounds of value in medical imaging. The technetium compound is combined in a mixture with non-growing microbial cells which contain a technetium-reducing enzyme system, a stabilizing agent and an electron donor in a saline solution under anaerobic conditions. The mixture is substantially free of an inorganic technetium reducing agent and its reduction products. The resulting product is Tc of lower oxidation states, the form of which can be partially controlled by the stabilizing agent. It has been discovered that the microorganisms *Shewanella alga*, strain Bry and *Shewanella putrifacians*, strain CN-32 contain the necessary enzyme systems for technetium reduction and can form both mono nuclear and polynuclear reduced Tc species depending on the stabilizing agent.

22 Claims, 3 Drawing Sheets

KIT FOR PROVIDING A TECHNETIUM MEDICAL RADIOIMAGING AGENT

CROSS REFERENCE TO RELATED INVENTION

This application is a Continuation-in-Part of application Ser. No. 09/099,680 filed Jun. 18, 1998, now abandoned.

This invention was made with Government support under Contract DE-AC0676RLO1830 awarded by the U.S. Department of Energy. The Government has certain rights in the invention.

FIELD OF THE INVENTION

The present invention is related to reducing pertechnetate. More specifically, it is related to a kit for microbial reduction of pertechnetate that is useful for medical imaging.

BACKGROUND OF THE INVENTION

Medical applications of Technetium (Tc) date from 1958 when the first Tc generator in convenient transportable forms was developed (Tucker, W. D., M. W. Greene, A. J. Weiss, and A. P. Murrenhoff. 1958. *Methods of Preparation of Some Carrier-Free Radioisotopes Involving Sorption on Alumina*. USAEC Report BNL-3746, Brookhaven National Laboratory, May 29, 1958). Technetium is produced primarily in the VII oxidation state (pertechnetate) in a column or solution through the decay of $Mo^{99}(VI)$ present as molybdate, without breakage of chemical bonds. Subsequent developments led to introduction in the mid-60's of a kit system in which the short-lived isotope of pertechnetate could be made available in sterile physiological saline as required for use on site.

Over 85% of routine human nuclear diagnostic procedures now rely upon $^{99m}Tc$ because of its excellent radiation characteristics (Jones, A. G. 1995. "Technetium in Nuclear Medicine." *Radiochimica Acta* 70/71:289–297), including (1) a half-life of 6.03 hr; (2) a 0.1405 MeV gamma ray photon that is almost totally absorbed by single, thallium-doped sodium iodide crystal slabs in cameras used for detection; (3) relatively little non-penetrating radiation (no beta particles and low energy auger electrons); and (4) decay to a long-lived groundstate ($^{99}Tc$) that is a low energy, beta emitter. These properties allow the use of higher doses while absorbed radiation dose is maintained at acceptable levels (Steigman, Joseph, and William C. Eckelman. 1992. *The Chemistry of Technetium in Medicine*. NAS-NS-3204, Nuclear Science Series, National Academy Press, Washington, D.C.). Thus, $^{99m}Tc$ offers properties nearly ideal for diagnostic tests, allowing short imaging times and clear images.

The combination of excellent imaging characteristics with the rich chemistry of Tc, which can assume oxidation states ranging from VII to 0 and coordination numbers from 4 to 9, has led to extensive research to find new compounds that target basic physiological functions, organs (e.g., liver, brain, heart, thyroid) and disease states. Research has focused on linking the radionuclide to delivery molecules of biological interest. Representative of this type of effort is the work of Hom, R. K., D. Chi, and J. A. Katzenellenbogen. 1995. "Stereochemical Issues in the Synthesis of bis-bidentate $(NS)_2$ Amino Thiol Complexes of Oxorhenium(V) and Oxotechnetium(V) whose Structures Mimic those of Steroids," pp. 441–434. In *Proceedings 11th International Symposium on Radiopharmaceutical Chemistry*, Vancouver, August 1995, to develop an agent for assessing breast cancer therapies in which the chelation chemistry of the element is exploited to develop desired in vivo properties, such as lypophilicity, charge and molecular structure.

The most oxidized state of Tc, the pertechnetate ion $[Tc(VII)O_4^{-1}]$, is the primary product of the nuclear production process. The pertechnetate ion itself is highly useful in imaging, but the range of lower oxidation states available for Tc offers a multitude of opportunities to form other chemical species, and the search for compounds of diagnostic value has focused principally on organic complexes with the lower Tc oxidation states. Thus, the reduction of pertechnetate becomes a critical step in exploitation of the full value of this element for diagnosis, in both (1) research to develop new inorganic or organic forms of Tc, and (2) commercial production of compounds that are proven to be of value.

Currently, to administer reduced forms of Tc for diagnostic purposes, the hospital technician usually purchases two kits. The first kit is a Tc generator which includes $Mo^{99}$ on a column that is "milked" for the $Tc^{99m}$, usually in the form of sodium pertechnetate. A second kit consists of a reaction vial containing, in lyophilized form and under a nitrogen atmosphere, a reducing agent and a complexing agent. Prior to lyophilization, the pH of the second kit is adjusted by the supplier to 4.0–7.5 with hydrochloric acid and sodium hydroxide. The addition of sodium pertechnetate to the second vial results in a chemical reaction reducing the pertechnetate to lower oxidation states that are stabilized in solution by reaction with the complexing agent before intravenous injection into a patient.

Presently, the inorganic compound tin chloride hydrate $(SnCl_2.2H_2O)$ is the chemical reducing agent used commercially. However, the complex chemistry of tin has produced a number of undesirable byproducts, including, e.g., excess Sn (II) ions, chlorocomplexes, polymers, colloidal Sn aggregates, "hydrolyzed" Tc and Tc complexes. In addition, excess Sn(II) and the Sn (IV) formed on reduction of Sn (II) complicate formation of the desired Tc complexes because they may form competing complexes (J. Steigman and W. C. Eckelman. 1992. The Chemistry of Technetium in Medicine. NAS-NS-3204, Nuclear Science Series, National Academy Press, Washington, D.C.) The presence of these byproducts has markedly hampered the development of test kits with reduced Tc compounds targeted for specific human organs and has spurred a 20-year search for other more satisfactory reducing agent(s). Other organic and inorganic reducing agents, such as sodium borohydride, hydrazine, hydroxiamine, ascorbic acid and sodium dithionite, have been the subject of extensive research as possible substitutes for Sn but each has disadvantages (e.g., dithionite decomposes in acid solutions) and result in complex chemical residuals that are generally unacceptable for human injection. Thus, there is a great need for new reductants for pertechnetate that offer less potential for toxic, complicated by-products and more potential for developing new Tc compounds for use in medical imaging.

In an unrelated art of environmental cleanup, investigators have suggested that environmental microrganisms may play a role in reduction of Tc in the geologic subsurface. Specifically, Wildung, R. E., K. M. McFadden, and T. R. Garland. 1979. Technetium Sources and Behavior in the Environment. *J. Environ. Qual.* 8:156–161 suggested that microbial processes may be involved in direct or indirect reduction of Tc in anaerobic soils and sediments. Further, Henrot, J. 1989a. Bioaccumulation and Chemical Modification of Tc by Soil Bacteria. In The Behavior of Technetium in Terrestrial and Aquatic Environs: A Symposium. R. E. Wildung, G. M. Desmet, D. A. Cataldo, and S. G Weiss, (Eds.). Health Physics 57:239–45; and Pignolet, L., Auvary, F., Fonsny, K., Capot, F., Moureau, Z. 1989b. Role of Various Microorganisms on Tc Behavior in Sediments. Health Physics 57:791–800, developed evidence that mixed cultures of anaerobic bacteria alter the solubility of Tc, initially added as pertechnetate, to solutions and marine sediments. D. R. Lovley.1993. Dissimilatory metal reduction. Annual Reviews of Microbiology 47:263–290 suggested that pertechnetate reduction offered a potential mechanism for removal of Tc from contaminated environments or waste streams. Presumptive evidence for the direct reduction of Tc in the environment has recently come from studies of Tc reduction by the isolated environmental bacteria *Shewanella putrifaciens, Geobacter metallireducens* (Lloyd, J. R., and L. E. Macaskie. 1996. "A Novel Phosphorlmager-Based Technique for Monitoring the Microbial Reduction of Technetium." *Applied and Environmental Microbiology* 62:578–582), *Chlostridium sphenoides* (Francis, A. J., C. J. Dodge, and G. E. Meinken. 1997. "Transformations of Technetium by Denitrifying and Fermentative Bacteria." In *Proceedings of 97th General Meeting of the American Society for Microbiology*, Q-271, Miami Beach, Fla., May 4–8, 1997), and *Shewanella alga* and *putrifacians* (S. W. Li, A. E. Plymale, Y. A. Gorby, J. K. Fredrickson, J. P. Mckinley, and R. E. Wildung. 1997. Reduction of Technetium by Dissimilatory Metal-Reducing Shewanelia sp. International Biometals Symposium. The University of Calgary, Aug. 10–14, 1997), and *Desulfovibrio desulfuricans* (J. R. Lloyd, H-f. Nolting, V. A. Sole, K. Bosecker, and L. E. Macaskie.1998. Technetium Reduction and Precipitation by Sulfate-Reducing Bacteria. Geomicrobiology Journal 15:45–58).

Although environmental microbial reduction of Tc has been suggested, there remains a critical need in the medical imaging art for a kit that results in reduced Tc with less chemical impurities.

SUMMARY OF THE INVENTION

The present invention is directed toward a kit for microbial reduction of a technetium compound for radioimaging. Specifically, the kit has:

(a) a first vessel, containing a technetium reducing microbe in;

(b) an aqueous solution; and (c) a separator for separation of a particulate-free solution containing a reduced technetium compound.

The kit may further include a second vessel containing a reducable technetium compound.

The separated product of reduced technetium compound is useful for medical radioimaging.

The technetium reducing microbe produces at least one enzyme capable of reducing technetium as may be found in a microbe or cells of a bacterium selected from the genus Shewanella sp. geobacter sp., Chlostridium sp., Desulfovibrio sp. and combinations thereof. Because these microorganisms reduce technetium under non-growth conditions, it is believed that the reduction is a direct enzymatic process by one or more enzymes. *Shewanella alga* (strain Bry) and Shewanella Sp. *putrifacians* (strain CN-32) were first demonstrated to reduce technetium by discovery according to the present invention.

The present invention has an advantage of using direct enzymatic reduction, a natural alternative to conventional pertechnetate reduction methods. The invention has been demonstrated with direct enzymatic reduction by viable, but non-growing, microbial cells of strains, specifically *Shewanella putrifaciens* strain CN 32 and *S. alga* strain Bry. Rapid reduction of pertechnetate to Tc in oxidation states (IV) and (V) in the saline solutions used in medical practice was observed. Depending upon the presence of inorganic and organic complexing agents, the process can form a range of products with potential value in targeting different tissues and organs in the human body ( J. R. Dilworth and S. J. Parrott. 1998. The Biomedical Chemistry of Technetium and Rhenium." *Chemical Society Reviews.* 29:43–55).

The reactions and products of the microbial reduction have been demonstrated in the absence and presence of the organic complexing agent diethylenetriamine pentaacetic acid (DTPA) and the inorganic complexing agent carbonate.

In addition to the discovery of a natural enzymatic process as an alternative for reduction of Tc for pharmaceutical purposes without toxic byproducts, the present invention includes discovery of the formation of useful and potentially useful Tc reduction products by these processes.

The present invention permits selecting combinations of the electron donor and/or the stabilizing agent in association with enzyme or microbe for reduction to form compounds that are of potential value in medical imaging without the by-products of traditional chemical synthesis methods.

The present invention has the advantages of relying upon a benign enzyme system for reduction that can be found in naturally occurring sources of microorganisms, and avoidance of inorganic reducing agents.

It is an object of the present invention to provide a kit for microbially reducing technetium for radioimaging.

The subject matter of the present invention is pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

The kit of the present invention for reducing a technetium compound for use in medical radioimaging, permits combining the technetium compound, microbe capable of direct microbial reduction of the technetium compound, a complexing agent to stabilize the lower oxidation state(s) of technetium formed by microbial reduction, and an electron donor in an aqueous solution as a mixture under anaerobic conditions, wherein the mixture is substantially free of an inorganic technetium reducing agent, and a reduced technetium compound is obtained. The reduced technetium compound is then separated from the technetium reducing microbe(s) by simple withdrawal of an aliquot of the suspension with either a standard small syringe containing a filter (capable of effective removal of particles less than 0.2 microns) or a centrifuge. Addition of microbe(s) and an electron donor to the remaining constituents of the mixture initiates the reduction process.

The technetium compound to be reduced is typically pertechnetate, but may be any reducible technetium compound including $Tc(VII)O_4^-$ (pertechnetate) $Tc(VI)$ or $Tc(V)$ and combinations thereof.

The microbe, particularly a microbe capable of reducing iron, is preferably Shewanella Sp. including *Shewanella putrifaciens* (CN-32), *Shewanella alga* (Bry); Geobacter Sp. including *Geobacter metallireducens*; Desulfovibrio Sp. including *Desulfovibrio desulfuricans*, Clostritium sp, including *Chlostridium sphenoides* and combinations thereof. Shewanella strains Bry and CN-32 were first demonstrated to unequivocally reduce technetium by discovery according to the present invention. These microorganisms occur in natural waters under anaerobic conditions and are of a group of dissimilatory iron reducing microorganisms that conserve energy for growth and reproduction in the environment by reduction of Fe(III) to Fe(II) using either $H_2$ or organic compounds (e.g., lactate) as electron donors. The end products of pertechnetate reduction by these microorganisms include only reduced Tc chemical species, and microbial cells when $H_2$ is used as the electron donor. If an organic compound is used as the electron donor, the products will additionally include any residual organic compound(s). Organic compound electron donors include but are not limited to carboxylic acid, for example lactate, acetate, formate and combinations thereof. This is a versatile, entirely natural Tc reduction process with no secondary products when $H_2$ is used as the electron donor and limited, non-toxic secondary products when an organic compound is used as the electron donor.

Figure 3:
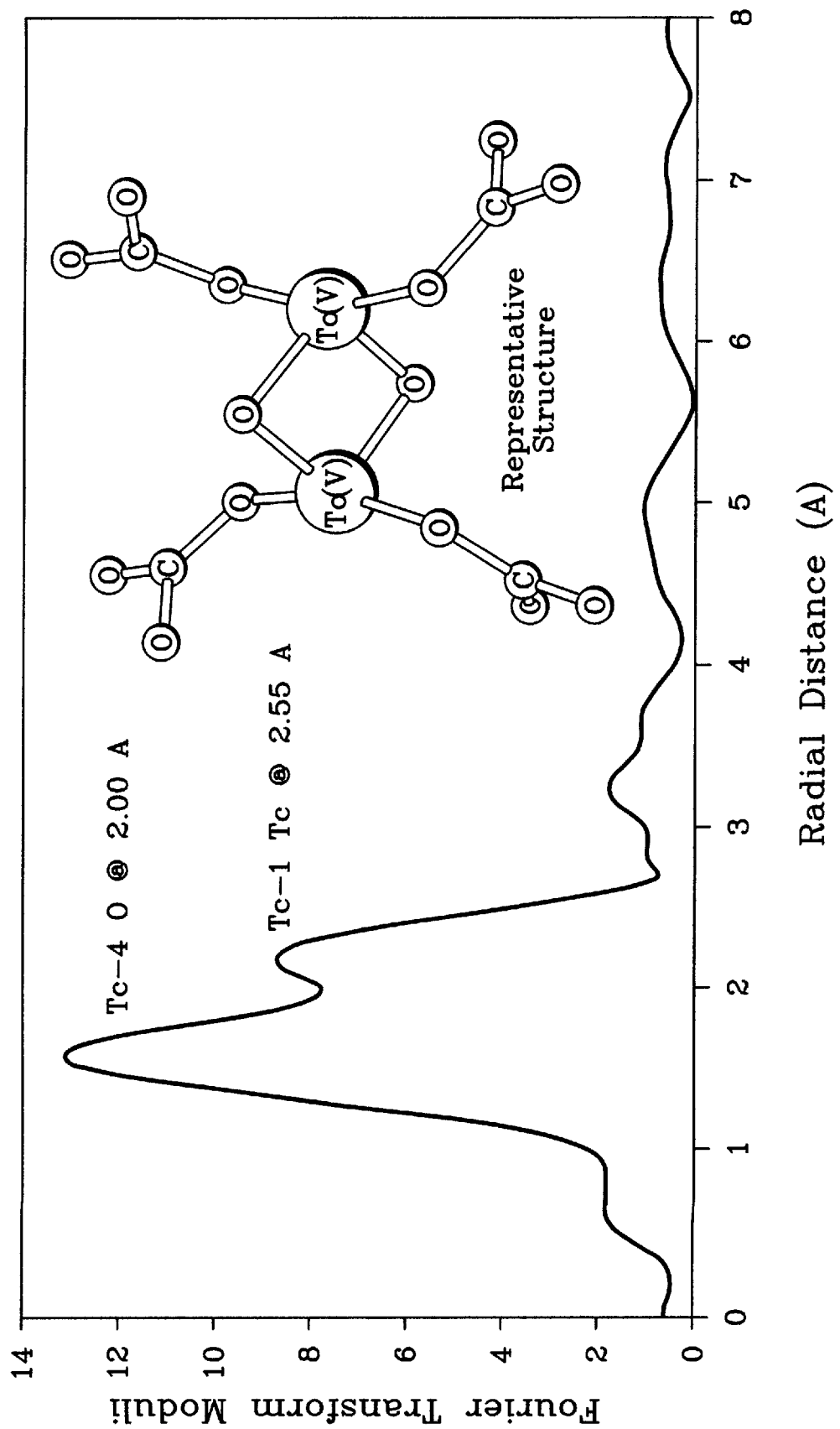
FIG. 3 is a graph of Fourier transform modulii versus radial distance superimposed with a representative structural model of the dimeric technetium/carbonate complex made with microbial enzymatic reduction.

The complexing agent may be a stable organic species, for example, diethylenetriamine pentaacetic acid (DTPA) commonly used in kit form to stabilize Tc (IV) obtained by reduction with SnCl2. However, there are many potential inorganic (e.g., bicarbonate, FIG. 3) or organic complexing ligands that may be employed to obtain a wide variety of reduced Tc complexes for versatile use in medical imaging. Examples of ligands that may be employed in this system include but are not limited to the amino carboxylates, thiols, polyhydroxy acids, and phosphonates identified in (Steigman, Joseph, and William C. Eckelman. 1992. *The Chemistry of Technetium in Medicine*. NAS-NS-3204, Nuclear Science Series, National Academy Press, Washington, D.C).

The electron donor may be hydrogen, or an organic compound, and combinations thereof.

Operating parameters are preferably ambient conditions of temperature, pressure, pH greater than 4 and less than 8, more preferably pH 6.0–7.5 and saline solutions all of which are ideal for intravenous injection. More extreme conditions may be tolerated within the survival or activity range of enzyme(s) or enzyme producing microorganisms. Anaerobic conditions are required for the microbial reduction, but once stabilized by reaction with a complexing agent, the reduced Tc compound is not restricted to the anaerobic conditions and can generally be handled and administered with procedures typically in use for compounds produced by other reducing agents. The microbial cells are preserved for use by standard methods of lyophilization which renders them stable for transport and handling under ambient conditions. The cells of Shewanella are activated on contact with the solution and facultatively anaerobic in that they can also use oxygen as an electron acceptor under aerobic conditions, removing any residual trace concentrations of oxygen in the reaction vessel, or, with the appropriate concentrations of electron donor and microbial cells, the organisms will be able to lower the concentration of $O_2$ in the atmosphere of a sealed reaction vessel from fully aerobic (8 parts per million) to virtually zero, eliminating the need for an anaerobic atmosphere.

The present invention is the first demonstration of microbial reduction of technetium to a polynuclear compound.

EXAMPLE 1

An experiment was conducted to demonstrate enzymatic technetium reduction.

*Shewanella alga* strain BrY and *S. putrefaciens* strain CN-32, facultative anaerobes were originally isolated from estuarine sediments by the methods set forth by Caccavo, F. Jr., R. P. Blakemore, and D. R. Lovley. 1992. A hydrogen-oxidizing, Fe(III)-reducing microorganism from the Great Bay Estuary, New Hampshire. *Applied Environmental Microbiology*. 58:3211–3216 and an anaerobic aquifer as by Balkwill, D. L. 1993. DOE makes subsurface cultures available. *American Society of Microbiology News* 59:504–506. The isolated facultative anaerobes were cultured aerobically in tryptic soy broth.

Cells were harvested after 16 h and washed with an anoxic, pH 7 solution of either 30 mM $NaHCO_3$ and 1.3 mM KCl (bicarbonate medium) or 0.85% NaCl (saline medium) and resuspended in either medium to a density of ~1×10$^8$ cells/ml.

Dissimilatory reduction of 100–500 $\mu$M Tc (added as $NH_4{}^{99}TcO_4$) was measured in 10-ml anoxic cell suspensions of the bicarbonate and saline media with either lactate (10 mM) or $H_2$ (10 ml) as the electron donor and in the presence and absence of 300 mM DTPA (saline medium only).

Filtered (0.2 and 0.01 $\mu$m) and unfiltered subsamples of the reaction mixtures were taken at various times with needle and syringe and stored anaerobically until assayed.

A reduced Tc(IV) control ($TcO_2$) was prepared by reduction with stannous chloride (Jackson, G. E., M. J. Byrne, H. Fakier, R. Hunter, and M. Woudenberg. 1994. Technetium-99m labeling of bis-oxime ligands. *Applied Radiation Isotopes* 45(5):581–586) in the presence and absence of DTPA (300 mM).

The distribution of $^{99}$Tc in filtered and unfiltered samples was determined by liquid scintillation counting (0.292 Mev, beta) or phosphor-imaging (Bio-Rad Laboratories).

Soluble (<0.2 $\mu$m) Tc species were (1) separated by paper electrophoresis (buffer: 30 mM $NaHCO_3$/1.3 mM KCl, pH 9.2; medium: cellulose acetate; conditions: 60 V, 1 h, anaerobic) and visualized and quantified by phosphor-imaging and (2) subject to x-ray absorption spectroscopy (extended x-ray absorption fine structure) at the Stanford Linear Accelerator Laboratory. Method (1) allows rapid separation and visualization of reduced technetium-containing components. Method (2) is a highly advanced technology for direct determination of technetium oxidation state and form.

Figure 1:
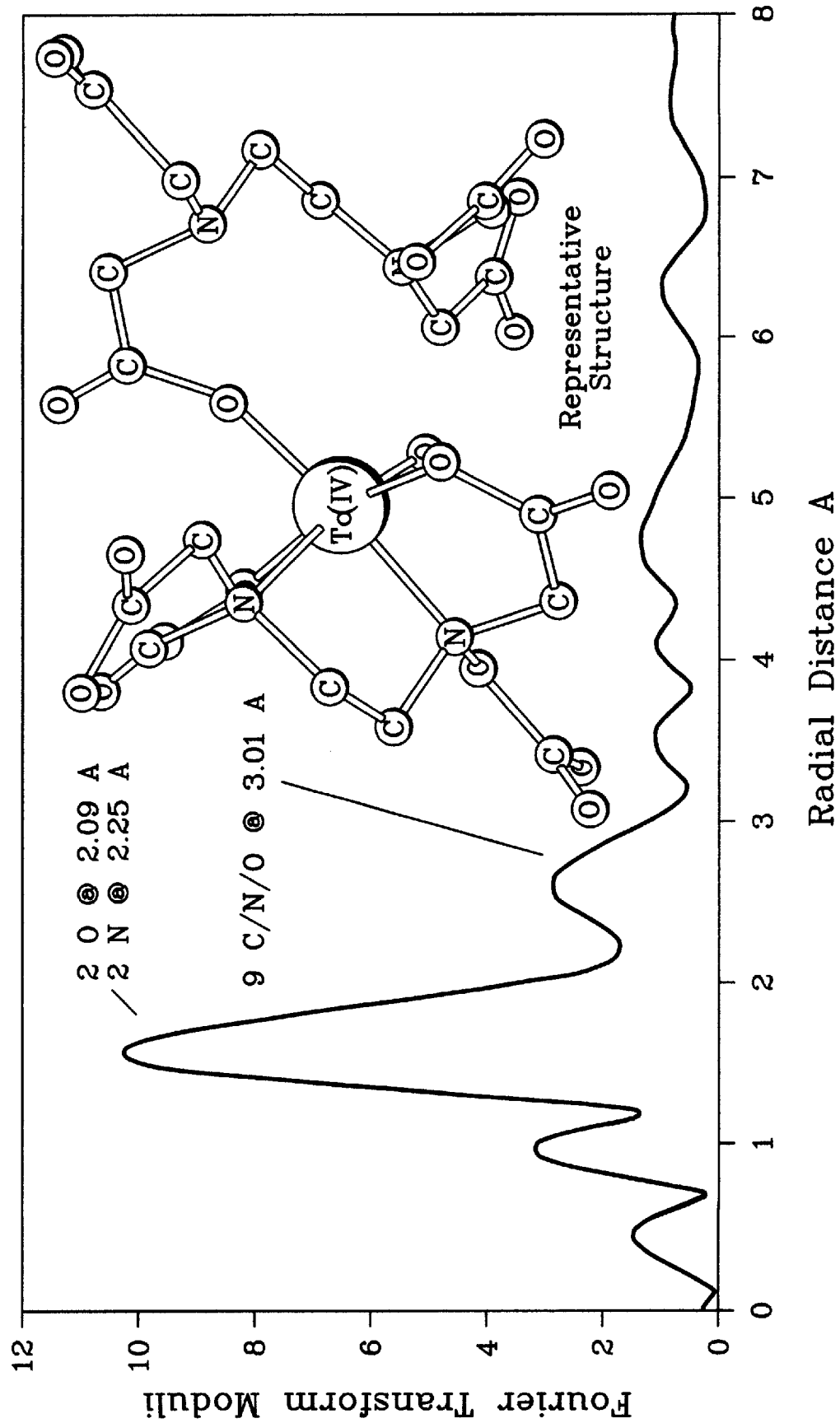
FIG. 1 is a graph of Fourier transform modulii versus radial distance superimposed with a representative structural model of the technetium/DTPA complex made with microbial enzymatic reduction.
Figure 2:
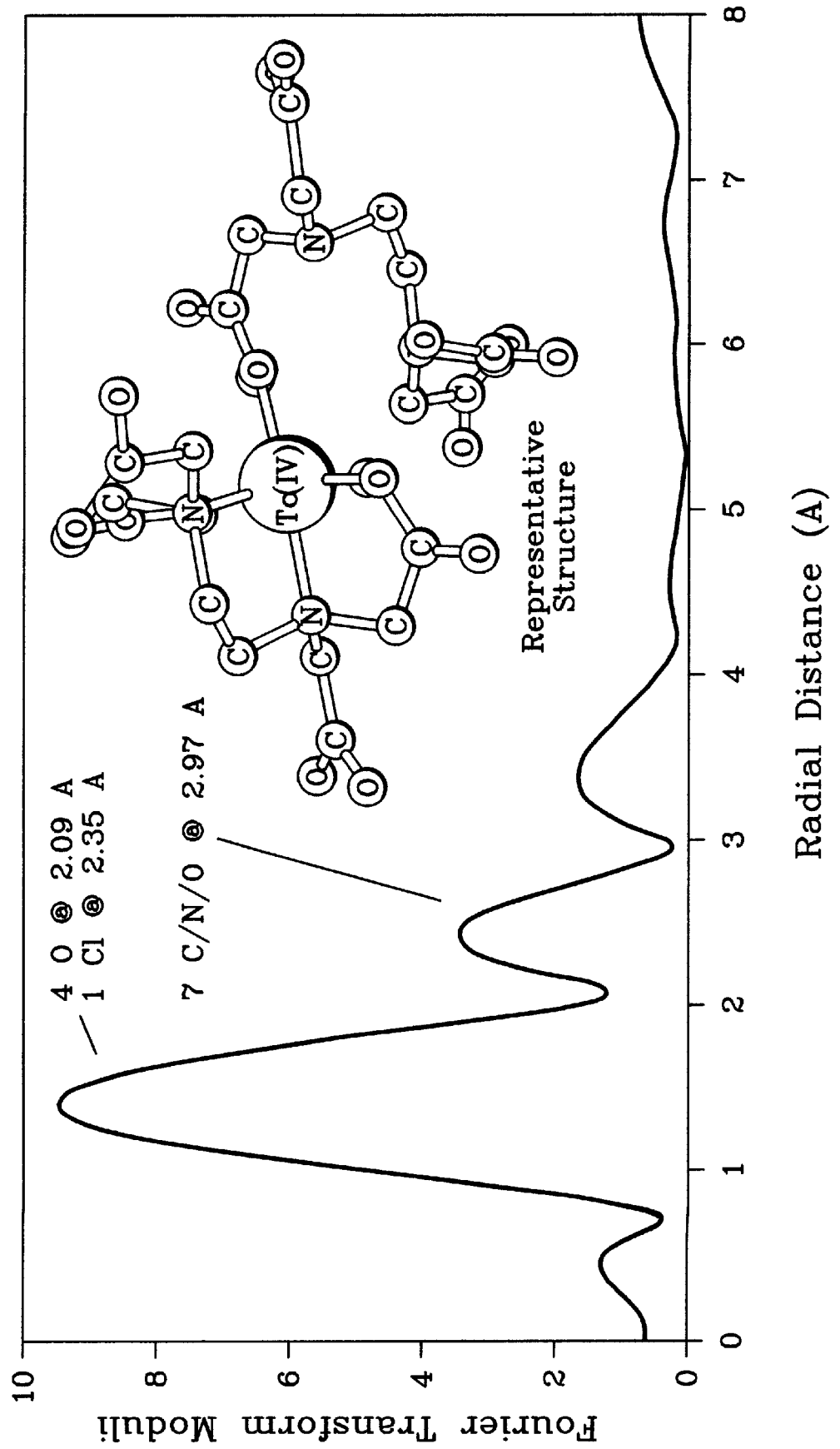
FIG. 2 is a graph of Fourier transform modulii versus radial distance superimposed with a representative structural model of the technetium/DTPA complex made with $SnCl_2$.

Results of x-ray absorption spectroscopy show the formation by microbial processes of soluble monomeric Tc (IV) DTPA complexes identical to those produced using the inorganic reductant SnCl2 (compare FIG. 1 and FIG. 2) but without the presence of excess Sn and without potential for formation of potentially toxic Sn products. In addition, it was discovered that substitution of carbonate as a complexing (or stabilizing) ligand resulted in a soluble polymeric Tc(V) carbonate complex as a reduction product (FIG. 3), offering new opportunities for development of a range of new Tc compounds for medical imaging research without Sn residuals and by products. Potential avenues for forming new compounds include use of different combinations of electron donors (changing the kinetics of the reaction) and of stabilizing agents present during microbial reduction. This experiment is extremely reproducible and has been replicated many times.

It was observed that Eh begins at approximately 0 mV and decreases to minus 250 mV for the lactate donor and minus 475 mV for the hydrogen donor.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A kit for radioimaging, comprising:
   (a) a first vessel, containing a technetium reducing microbe in an aqueous solution;
   (b) a second vessel containing a reducable technetium compound; and
   (c) a separator for separation of a particulate-free solution containing a reduced technetium compound.

2. The kit as recited in claim 1 wherein said aqueous solution is a saline solution.

3. The kit as recited in claim 1, wherein said aqueous solution contains an electron donor.

4. The kit as recited in claim 3, wherein said electron donor is selected from the group consisting of hydrogen, organic compound and combinations thereof.

5. The kit as recited in claim 4, wherein said organic compound is selected from the group consisting of lactate, formate, acetate and combinations thereof.

6. The kit as recited in claim 1 wherein said aqueous solution contains a complexing agent.

7. The kit as recited in claim 6, wherein said complexing agent is an organic complexing ligand.

8. The kit as recited in claim 7, wherein said organic complexing ligand is selected from the group consisting of soluble diethylenetriamine pentaacetic acid (DTPA), amino carboxylates, thiols, polyhydroxy acids, phosphonates and combinations thereof.

9. The kit as recited in claim 6, wherein said complexing agent is carbonate.

10. The kit as recited in claim 1, wherein said technetium reducing microbe is selected from the group consisting of Shewanella sp., Geobacter sp., Desulfovibrio sp. Clostritium sp. and combinations thereof.

11. The kit as recited in claim 10, wherein said Shewanella sp. is selected from the group consisting of *Shewanella putrifaciens, Shewanella alga* and combinations thereor.

12. The kit as recited in claim 10, wherein said Geobacter sp. is *Geobacter metallireducens*.

13. The kit as recited in claim 10, wherein said Desulfovibrio sp is *Desulfovibrio desulfuricans*.

14. The kit as recited in claim 10, wherein said Clostritium sp. is *Chlostridium sphenoides*.

15. The kit as recited in claim 1, wherein said separator is a self filtering syringe.

16. The kit as recited in claim 1, wherein said separator is a centrifuge.

17. The kit as recited in claim 1, wherein said reducable technetium compound is seleted from the group consisting of $Tc(VII)O_4^-$ (pertechnetate) Tc(VI), Tc(V) and combinations thereof.

18. A kit for radioimaging, comprising:
   (a) a first vessel, containing a technetium reducing microbe in;
   (b) an aqueous solution; and
   (c) a separator for separation of a particulate-free solution containing a reduced technetium compound.

19. The kit as recited in claim 18, further comprising:
   a second vessel containing a reducable technetium compound.

20. The kit as recited in claim 18, wherein said separator is a self-filtering syringe.

21. The kit as recited in claim 18, wherein said separator is a centrifuge.

22. The kit as recited in claim 18, wherein said aqueous solution is a saline or a carbonate solution.

* * * * *